United States Patent [19]
Ljungmann

[11] Patent Number: 6,017,495
[45] Date of Patent: Jan. 25, 2000

[54] STAINING APPARATUS FOR STAINING OF TISSUE SPECIMENS ON MICROSCOPE SLIDES

[76] Inventor: Torstein Ljungmann, Geitmyrsvn. 5, 0171 Oslo, Norway, 0171

[21] Appl. No.: 09/078,825

[22] Filed: May 14, 1998

Related U.S. Application Data

[63] Continuation of application No. PCT/NO96/00270, Nov. 15, 1996.

[30] Foreign Application Priority Data

Nov. 17, 1995 [NO] Norway ................................... 954650

[51] Int. Cl.[7] .................................................. G01N 35/10
[52] U.S. Cl. ............................. 422/65; 422/63; 422/104; 118/423; 118/500; 294/67.3; 436/43; 436/46; 436/47; 436/48
[58] Field of Search .................................. 422/99, 63, 65, 422/67, 100; 73/864.01; 118/300, 58, 59, 423, 500; 427/4; 436/46, 63, 174, 180, 67, 48; 294/67.3

[56] References Cited

U.S. PATENT DOCUMENTS 5,023,187  6/1991  Koebler et al. .......................... 436/180
5,417,576  5/1995  Hill .......................................... 435/299
5,439,649  8/1995  Tseung et al. ............................. 422/99

*Primary Examiner*—Long V. Le
*Attorney, Agent, or Firm*—Baker & Botts, L.L.P.

[57] ABSTRACT

A staining apparatus for staining of tissue specimens placed on microscope slides comprises a number of staining stations (4) and other working stations (1, 2, 3), where the staining stations (4) receive vessels (5) having liquid baths for receiving baskets containing microscope slides with the topical specimens, and a transport mechanism (17–20) having a hoisting device (17) arranged to be moved over the vessels (5) and to place baskets in or take these up from the vessels, and to transfer the baskets between the working stations (1–4) in accordance with a programme-controlled staining process. The vessels (5) are transparent and are arranged in a number of horizontal rows placed above one another on a stepped base like a tribune, the tribune having a gradient allowing visual inspection of the individual vessels (5) at the working stations (4) from a place of view in front of the apparatus.

10 Claims, 5 Drawing Sheets

STAINING APPARATUS FOR STAINING OF TISSUE SPECIMENS ON MICROSCOPE SLIDES

This is a continuation of copending international application No. PCT/NO96/00270 filed Nov. 15, 1996 designating the United States.

The invention relates to a staining apparatus for staining of tissue specimens placed on microscope slides, comprising a number of working stations of which some are staining stations receiving vessels having liquid baths for receiving baskets containing microscope slides with the topical specimens, and a transport mechanism having a hoisting means arranged to be moved over the vessels and to place baskets in or take these up from the vessels, and to transfer the baskets between the working stations in accordance with a programme-controlled staining process.

In microscopic examination of cell and tissue specimens it is necessary with a preparation of the specimens in accordance with certain mutually dependent working steps. After fixation and embedment of the specimens, the specimen blocks must be cut. In order to enable an easy microscopic examination, the embedment medium must be removed, and thereafter the specimens are stained. The purpose of the histological staining is to get an insight in the structure of the tissue and to distinguish between the components of the tissue. For this purpose it is important that the different dyes show affinities to specific tissue elements.

Previously known staining apparatuses of the above-mentioned type are able to carry out routine as well as special staining processes in the histological and cytological field, whereby the processes are carried out automatically, the processes being programmed in advance in accordance with the topical process conditions. The known staining apparatuses comprise a number of working stations which are arranged in one horizontal plane, in one or more rows, or in a circle.

This planar station arrangement results in that the known staining apparatuses are relatively space-demanding and unsurveyable. In addition to the fact that it is not possible to inspect the individual vessels and the liquid content or bath thereof without withdrawing the vessels manually from the apparatus, also the withdrawal and placing operations are relatively troublesome and difficult, since spill of liquid from the vessels must be avoided and especially the vessels in the innermost row are difficult to access. Moreover, in such operations the operator may also easily be exposed to harmful fumes from the bath solutions in the vessels.

It is an object of the invention to provide a staining apparatus which is constructed so as to give a maximum insight in and survey of the process progress and the baths.

Another object is to provide a staining apparatus wherein the accessibility to baths and baskets, for example in case of operational disturbances, is radically improved in relation to the known apparatuses, and wherein also the accessibility in emptying and filling of the vessels is correspondingly improved.

A further object of the invention is to provide a staining apparatus which has a compact construction and is not very bulky.

A further object is to provide a staining apparatus having a high production capacity and which is functionally efficient and reliable, at the same time as it can be built to a competitive price.

For the achievement of the above-mentioned objects there is provided a staining apparatus of the introductorily stated type which, according to the invention, is characterized in that the vessels are transparent and are arranged in a number of horizontal rows placed above one another on a stepped base like a tribune, the tribune having a gradient allowing visual inspection of the individual vessels on the working stations from a place of view in front of the apparatus.

The invention will be further described below in connection with an exemplary embodiment with reference to the drawings, wherein FIG. 1 shows a perspective view of a staining apparatus according to the invention;

Figure 1:
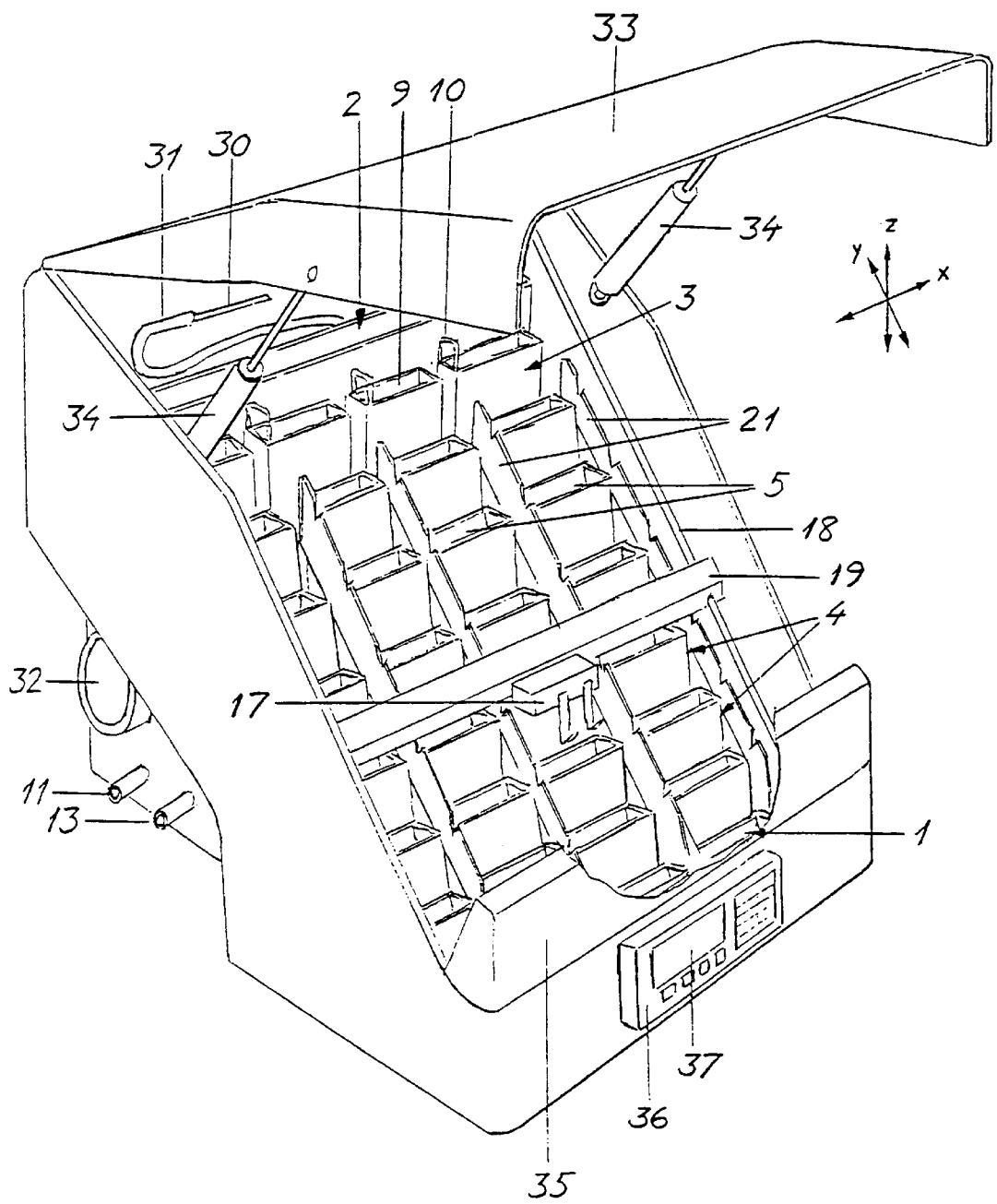

The staining apparatus shown in FIG. 1 is constructed to be able to carry out all types of routine and special staining processes within the field of histology and cytology. In the illustrated embodiment the apparatus includes 36 working stations, but this number can be increased, for example to 50 stations. The stations may e.g. comprise four to five fetching/unloading stations, four to five waiting/stove stations, four to five water rinsing stations and twenty to thirty staining stations. In FIG. 1, said station types—in the above-mentioned order—is designated by the reference numerals 1, 2, 3 and 4. Each of the staining stations 4 receives a container or vessel 5 having a dyeing bath 6 (see FIG. 2) for the reception of baskets 7 containing microscope slides with the topical tissue specimens. In a corresponding manner vessels 8 for input and output of baskets are arranged at the fetching/unloading stations 1, and on the rinsing stations 3 there are arranged suitable containers or vessels 9 for rinsing water baths. Rinsing water is supplied to the vessels 9 via water filling pipes 10 communicating with a water intake 11. Further, in connection with the vessels 9, there is arranged a drain hose 11 for drainage of sprinkling water from the rinsing baths. This hose is connected to a water outlet 13.

As shown, the waiting/stove stations 2 are shaped as an upwardly open casing 14 having an upper edge for the support of slide baskets 7 in a number of stove positions corresponding to the individual stations. The stations are heated by means of hot air supplied from a fan 15 in combination with a heating element (not shown).

As regards the staining stations, these may also comprise treatment stations which are not actual staining stations, but which contain chemical baths for other preparation of the tissue. Thus, with "staining stations" there are meant liquid stations containing chemicals staining or preparing the tissue for dyeing.

In accordance with the invention, the apparatus is constructed with the vessels 5, 8, 9 arranged in a number of horizontal rows placed above one another on a stepped foundation or base 16 like a tribune. The vessels are made of a transparent material, e.g. glass. The tribune has a gradient allowing visual inspection of the individual vessels from a place of view in front of the apparatus. This arrangement gives the operator a substantially better survey of the baths and the process as a whole than the previously known flat constructions, at the same time as the transparent vessels have the effect that one can assess in a simple manner the liquid condition in the individual baths. In addition there is achieved an ergonomic profit with manual transport of the baths into and out of the apparatuses.

The transport mechanism of the apparatus includes a hoisting means 17 which is arranged to be moved over the vessels and to place baskets in or take these up from the vessels, and to transfer the baskets between the working stations in accordance with a pre-programmed staining process. The transport mechanism comprises a hoist guiding means comprising a pair of guide rails 18 extending between the upper and lower ends of the tribune 16 on each side thereof and having a gradient corresponding to the tribune gradient, each of the rails 18 supporting a carrier bracket 19 driven along the rail for a traverse-screw and shaft means, for support and transverse movement of the hoisting means 17. The drive means for the brackets 19 is not further shown, but this may consist of a conventional screw or toothed belt means. Thus, by means of the transport means, the baskets can be moved in both the x, the y and the z direction depicted in FIG. 1.

As appears from FIG. 1, the shown embodiment of the staining apparatus is based on a ramp-shaped tribune. It is to be remarked, however, that one can also imagine an embodiment wherein the tribune base has a shape corresponding to a truncated cone, so that the tribune will then comprise a number of circular rows arranged above each other. In such an embodiment the tribune base will be rotatable about the cone axis, so that the transport mechanism does not need to move the hoisting means in the above-mentioned x direction, but only in the y and z directions.

Figure 3:
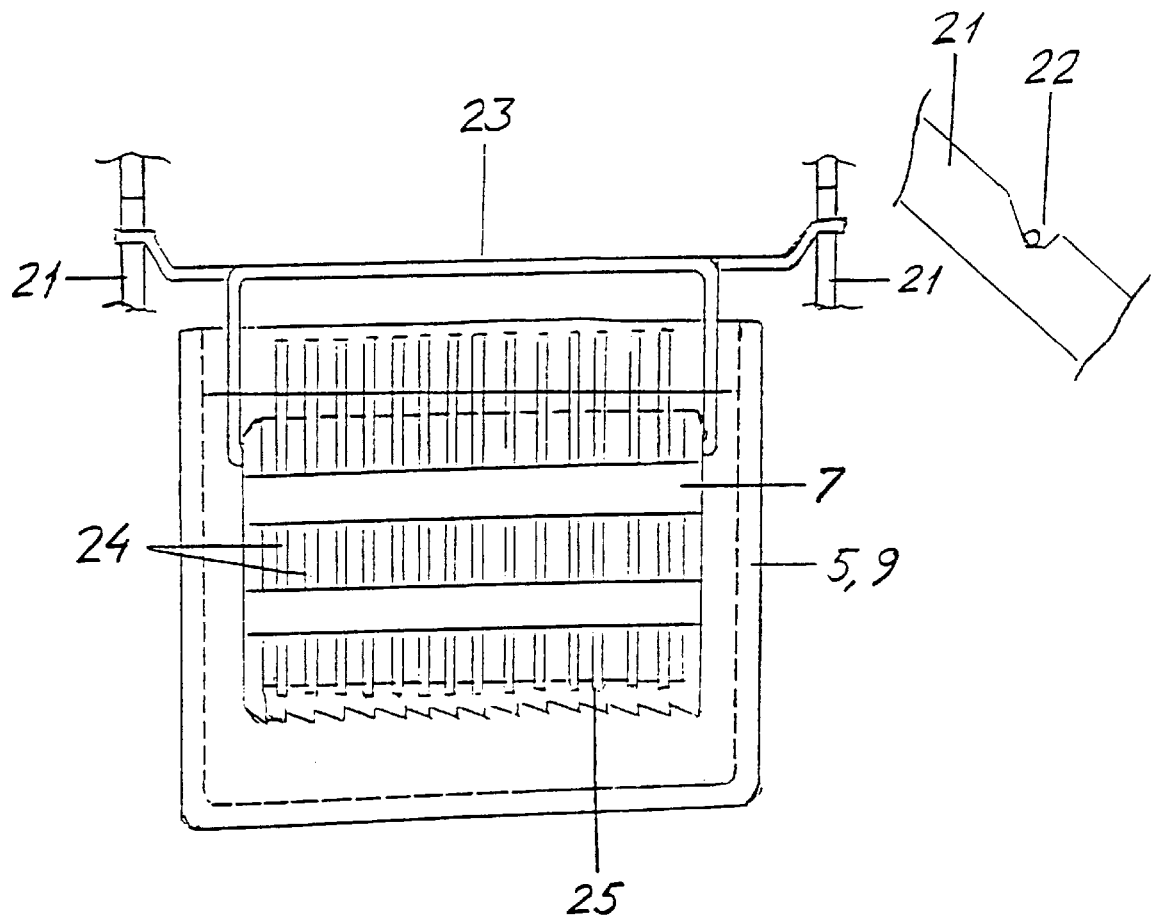
FIG. 3 shows a side view of a basket having microscope slides inserted therein.
Figure 4:
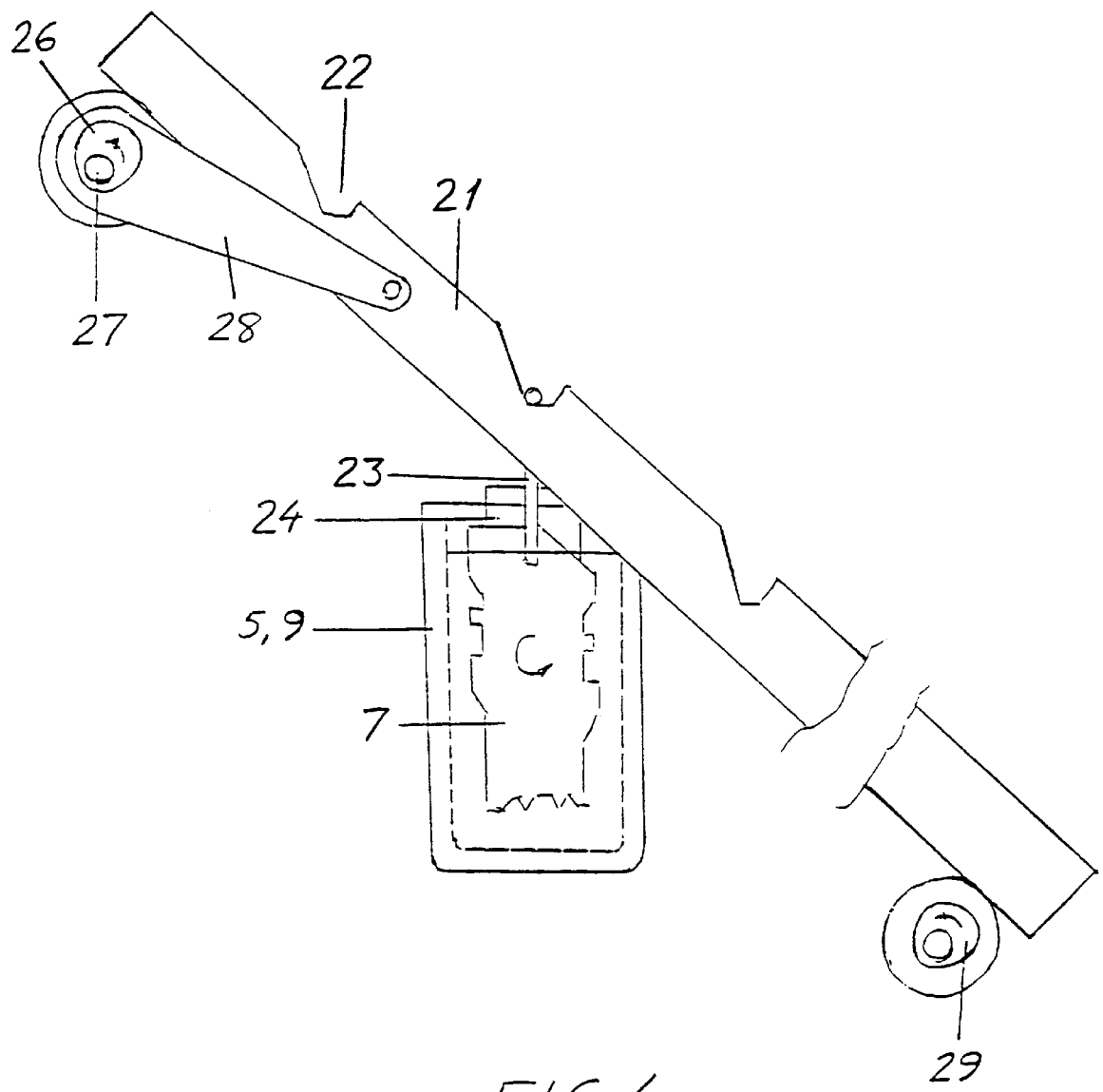
FIG. 4 shows a support rail with an associated eccentric means forming part of an agitating means for slide baskets.

For the achievement of an efficient dyeing and rinsing of the tissue specimens on the microscope slides, there is provided a means for agitating the slide baskets 7 which are placed in the dyeing baths/chemical baths and the rinsing baths. In the present apparatus the agitating means is common to all of these baskets. The means comprises a framework having a number of support rails 21 (omitted in FIG. 2) extending along and on each side of ascending rows of vessels 5, 9 and being arranged for support of the baskets 7 in the respective rows. One of the support rails 21 is partly shown in FIG. 4. As shown, the rail at its upper edge is provided with a number of V-shaped notches 22 for the support of a wire suspension 23 (e.g. of stainless steel) which is mounted at the top of the baskets 7. An embodiment of the wire suspension 23 is shown in FIG. 3 which also shows a plurality of microscope slides 24 inserted in the basket 7. The shown basket may also be designated a cassette in which the microscope slides are inserted in respective holding grooves 25 in the sides and bottom of the cassette.

The support rails 21 are supported at one end by an eccentric disc means 26 which is rotated by a motor-driven shaft 27, and which is also connected to one end of an arm 28 which, with its other end, is articulated to the support rail 21 to give the rail a reciprocating movement at the same time as it is lifted and lowered by rotation of the eccentric disc. At its other end, the support rail 21 is supported by a corresponding eccentric disc means 29 which is rotated synchronously with the first-mentioned means 26. Rotation of the eccentric disc means thus causes the rails 21 and therewith the baskets 7 to be lifted and lowered in a circulating movement.

All the automatic movements of the driving and operating elements of the apparatus are effected by small electric motors which are not shown in the schematic drawings.

The liquid-filled vessels 5 at the dyeing stations will also be provided with lids (not shown) which are arranged to be opened and closed automatically by a suitable motor means. The vessels may be provided with individual lids, or the vessels in a horizontal row alternatively may be provided with a common lid. By means of such lids dripping from baskets into baths which are not in use is prevented, and in addition evaporation from the baths is restricted.

Figure 5:
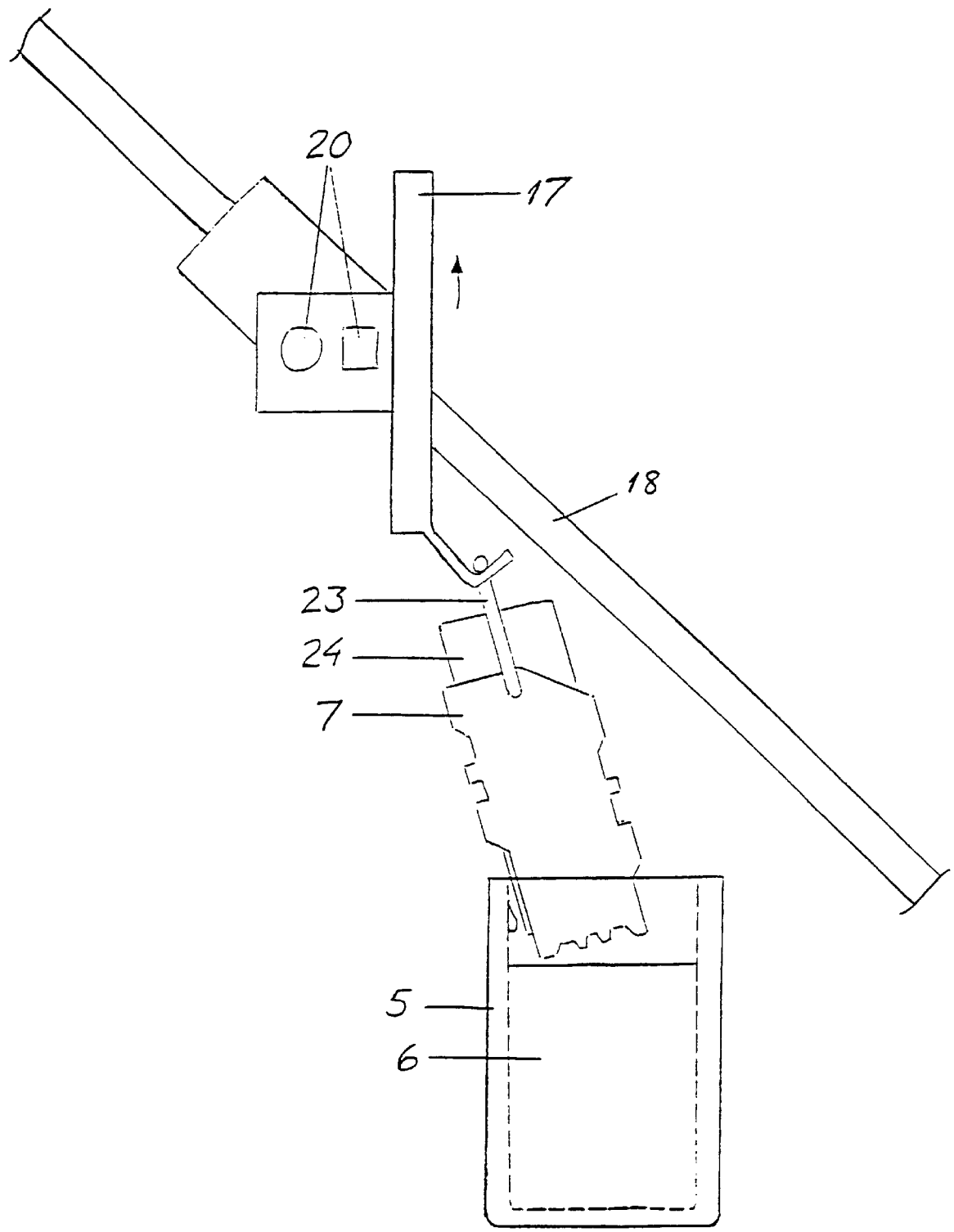
FIG. 5 is a view illustrating taking-up of a slide basket from a liquid bath in a vessel.

As shown in FIG. 5, the hoisting means 17 in its stop position at the dyeing stations is somewhat laterally displaced in relation to the vessels 5 in the station row in question. This results in that a slide basket 7, when this is taken up from a bath 6 after an accurately programmed time, is guided along a side edge of the vessel 5 or of the lid thereof, so that the adjacent side edges of the microscope slides 24 stroke against the edge and superfluous liquid on the slide thereby is "scraped" off and runs into the vessel again. The purpose of this provision is to preserve the liquids in the baths and simultaneously restrict the contamination from one bath to another.

For emptying of exhausted or contaminated baths, the apparatus is provided with a suction and drainage means. This consists of a suction head 30 and a hose 31, as shown in FIG. 1. Thus, the baths normally can be emptied by this means, so that one is let off lifting out full baths with the risk of soiling and direct contact with the chemicals. The hose is arranged in such a manner that it can lead the liquid to individual vessels as desired, for regeneration, waste treatment, etc. Thus, the arrangement enables an environmentally friendly and operator-friendly collection and sorting of different, more or less harmful chemicals, and also that one is let off soiling and direct contact, as with manual emptying of the vessels. Also in this connection the tribune design makes it simple to see the liquid level in the vessels, settlings at the vessel bottom etc. The vessels are formed with a slightly slanting bottom and a sump, so that the emptying by means of the suction head becomes as efficient as possible.

Figure 2:
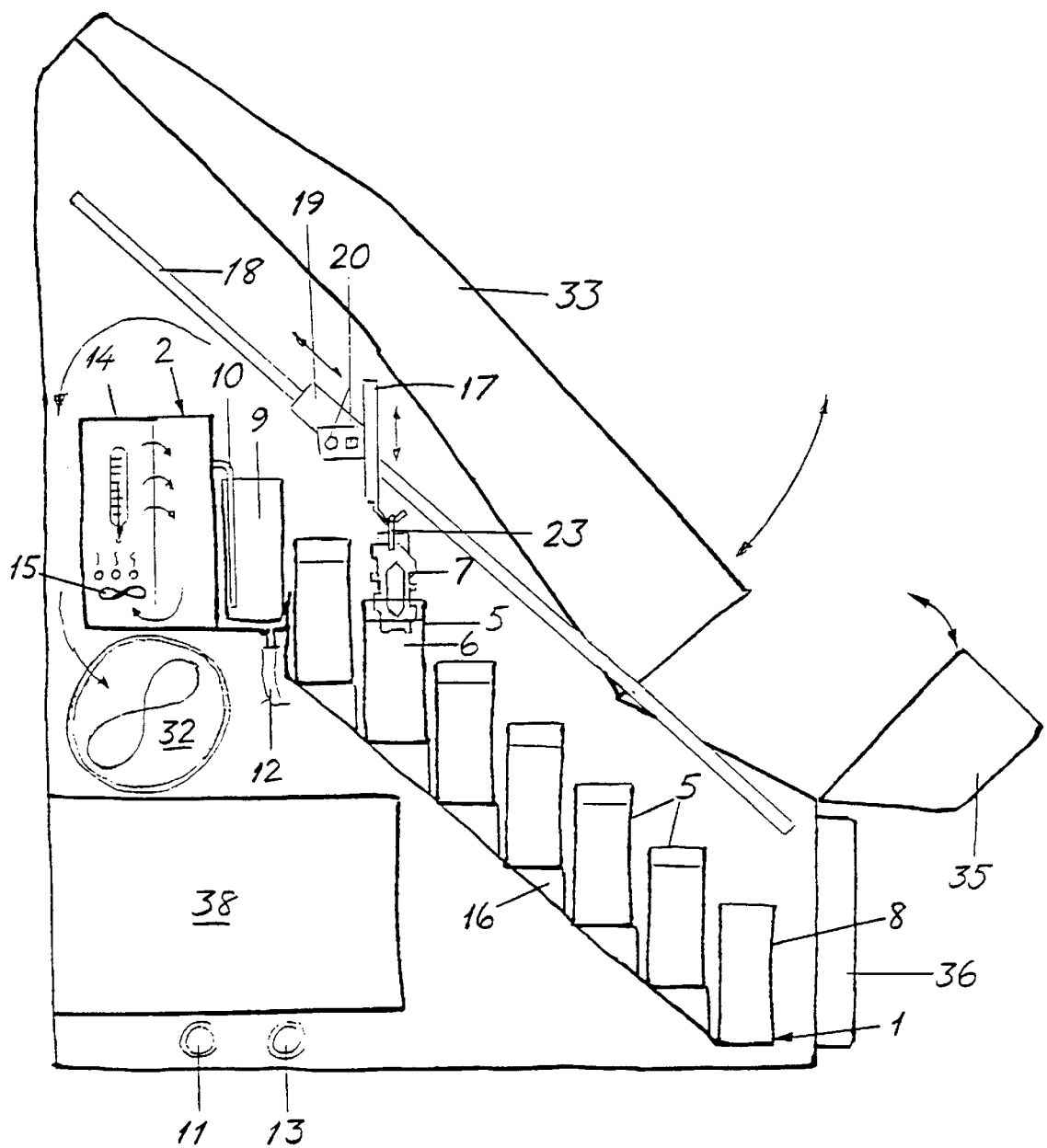
FIG. 2 shows a schematic, sectional side view of the apparatus in FIG. 1.

As suggested in FIGS. 1 and 2, the apparatus is also provided with a sucking-out means 32 comprising a ventilating fan which is combined with a filter system for absorption of gases from solvents. The apparatus has a main cover 33 which is hinged at the upper rear edge of the apparatus and in addition is coupled to a pair of gas damping cylinders 34. Further, the apparatus has a front cover 35 and an operating panel 36 with a display 37 arranged in the central area thereof. This gives a simple use and a logical communication with the operator.

As a result of the tribune design there is also obtained a compact construction wherein the apparatus has a low constructional height at the front and wherein the component parts of the apparatus, i.e. mechanical, electrical and electronic working components, which are not located at the upper side of the tribune, are arranged in the "vacant" space which is present under the tribune. As shown in FIG. 2, this space inter alia receives a junction box 38 which is fixed to a rear wall of the apparatus and which contains the current inlet means, electronic units, etc. of the apparatus. The apparatus is connected to the topical mains voltage (110 V AC–60 Hz or 230 V AC–50 Hz) which is transformed down to an operating voltage of 24 volts. The electronic units, which are based on microprocessor technology, controls the operation of the apparatus in accordance with the topical programme. The apparatus has a memory (EEPROM) in which there may be stored up to 32 different programmes. Up to three different programmes can be in operation simultaneously. The electronic units give the possibility for print-out of staining or dyeing programme and baths conditions. Further, there is a possibility for automatic warning of dyeing bath conditions. For this purpose there will be built in a device for indication of a signal for exchange of a bath after immersion of slide baskets a certain number of times in the bath. The signal for the topical bath is delivered in dependence on a so-called "wear factor" which can be programmed individually for the different dyeing baths. This is a substantial advantage with respect to flexibility, as one may then have control with the extent of wear of the different types of dyeing baths used in the vessels, according to the chosen programme. If desired, also the dyeing time can be varied automatically by means of this wear factor.

I claim:

1. A staining apparatus for staining of tissue specimens placed on microscope slides, comprising:

a base having a front and a rear and a plurality of horizontal steps, each of the steps in a direction from the front to the rear of the base being at a successively greater height relative to a lowest front step and being arranged at a gradient so as to enable a user to view work stations on each step from a vantage point in front of the apparatus;

a plurality of work stations arranged in a row on each step of the base, a majority of the steps of the base having staining stations receiving transparent vessels having liquid baths for receiving baskets containing the microscope slides, and a transport mechanism having hoisting means for moving over the vessels and for placing baskets in and taking baskets out of the vessels and for transferring the baskets between said working stations in accordance with a program-controlled staining process.

2. The staining apparatus according to claim 1, wherein the steps of the base have, in ascending succession from the front to the rear:

work stations with vessels for input and output of baskets on the lowest front step, staining stations on a plurality of steps, rinsing stations on one step, and stove stations for drying of the tissue specimens on the microscope slides on an uppermost step.

3. The staining apparatus according to claim 1, wherein said vessels at the staining stations are provided with lids arranged for automatic opening and closing.

4. The staining apparatus according to claim 1, and further comprising a common agitating means for imparting motion to all of said baskets that are placed in said vessels at the staining stations.

5. The staining apparatus according to claim 4, wherein said agitating means comprises a framework having a number of support rails extending along and on each side of ascending rows of vessels, and which are arranged for support of the baskets in respective rows, said support rails at each end being connected to synchronously-driven eccentric disc means which upon rotation cause the rails and therewith the baskets to be lifted and lowered in a circulating movement.

6. The staining apparatus according to any one of claims 1–5, wherein said hoisting means comprises a pair of guide rails extending between the front and the rear of the base at each side thereof and having a gradient corresponding to the gradient of the base, each rail supporting a carrier bracket driven along the rail and carrying a traverse-screw and shaft means for imparting transverse movement to the hoisting means.

7. The staining apparatus according to any one of the claims 1–5, wherein said hoisting means in a stopped position at the staining stations is laterally displaced relative to the vessels at the staining stations so that said baskets, when lifted out of the respective vessels, are guided along a side edge of the vessel or of a lid on the vessel, so that adjacent side edges of the microscope slides stroke against said side edges, whereby superfluous liquid on the slides thereby runs into the vessel again.

8. The staining apparatus according to any one of the claims 1–5, further comprising a suction and drainage means for emptying and drainage of liquid from vessels at the staining stations.

9. The staining apparatus according to any one of the claims 1–5, wherein mechanical, electrical, and electronic working components of the apparatus that are not located at the rear of the base are arranged in a space under the base.

10. The staining apparatus according to any one of the claim 1–5, and further comprising a means for delivery of a signal for exchange of a liquid bath after immersion of baskets a chosen number of times in the bath, said signal for the liquid bath being delivered in dependence upon a wear factor that can be programmed individually for each of the liquid baths in the different vessels.

* * * * *

UNITED STATES PATENT AND TRADEMARK OFFICE
CERTIFICATE OF CORRECTION

| | | |
|---|---|---|
| PATENT NO. | : 6,017,495 | |
| APPLICATION NO. | : 09/078825 | |
| DATED | : January 25, 2000 | |
| INVENTOR(S) | : Torstein Ljungmann | |

It is certified that error appears in the above-identified patent and that said Letters Patent is hereby corrected as shown below:

<u>Title Page, Item [56]</u> References Cited, U.S. PATENT DOCUMENTS: under "Tseung et al. .....422/99" insert --4,911,098    3/1990    Tabata

FOREIGN PATENT DOCUMENTS

2605105    10/1986    France --.

Signed and Sealed this

Seventeenth Day of July, 2007

JON W. DUDAS
*Director of the United States Patent and Trademark Office*